United States Patent [19]
Abramitis

[11] 4,071,348
[45] Jan. 31, 1978

[54] PLANT GROWTH CONTROL
[75] Inventor: Walter W. Abramitis, Downers Grove, Ill.
[73] Assignee: Akzona Incorporated, Asheville, N.C.
[21] Appl. No.: 348,390
[22] Filed: Apr. 5, 1973
[51] Int. Cl.$^2$ .......................... A01N 5/00; A01N 9/24
[52] U.S. Cl. ........................................... 71/78; 71/106
[58] Field of Search ............................................ 71/78
[56] References Cited
U.S. PATENT DOCUMENTS

| | | | |
|---|---|---|---|
| 2,603,560 | 7/1952 | Stewart | 71/77 |
| 3,223,517 | 12/1965 | Abramitis et al. | 71/78 |
| 3,438,765 | 4/1969 | Iso et al. | 71/78 |
| 3,506,433 | 4/1970 | Abramitis et al. | 71/78 |
| 3,810,750 | 5/1974 | Davidson et al. | 71/78 |

FOREIGN PATENT DOCUMENTS 46,273  10/1968  Japan ....................................... 71/78

OTHER PUBLICATIONS

Steffens, et al., J. Agr. Food Chem., vol. 17, No. 2, (1969), pp. 312–317.

Primary Examiner—Lewis Gotts
Assistant Examiner—Catherine L. Mills
Attorney, Agent, or Firm—Francis W. Young; Hugo E. Weisberger

[57]     ABSTRACT

The control of undesirable secondary growth in plants is accomplished by applying thereto a composition comprising a monoalkyl ester of a dibasic acid (e.g., succinic acid) and a surface active agent.

17 Claims, No Drawings

PLANT GROWTH CONTROL

BACKGROUND OF THE INVENTION

Relevant prior art is disclosed in U.S. Pat. Nos. 3,506,433; 3,223,517; and 2,603,560.

In various plants, such as, for example, tobacco, tomato, cotton, soybean plants, etc., undesirable secondary growth, which is generally referred to as "suckers", creates a serious problem because the suckers develop rapidly to shade desired portions of the plant, compete for the nutrients, and tend to ruin the quality of such desired portions. In the tobacco plant, secondary buds form at the points where the leaf stems join the plant, and later after the flower is removed grow rapidly to form sucker growths extending over the leaves. The sucker growths can be removed manually, but this is a laborious and expensive proceeding. The use of sucker oil and chemicals, while effective in control of such secondary growth, nevertheless have in the past had serious disadvantages. The sucker oil tends to form leaf and stalk damage, causing soft spots that are attacked by microbes, and also there is a lack of control of the lower sucker stalks. The chemicals which have previously been used produce cellular changes in the leaf tending to reduce the filling capacity of the treated tobacco for cigarette manufacture. Further, the cost of the chemicals has been high.

DESCRIPTION OF THE INVENTION

The composition of the invention, which is applied to plants to avoid the above disadvantages, comprises a long-chain monoalkyl ester of a dibasic organic acid having three or four carbon atoms in the acid residue and having the formula:

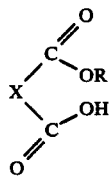

wherein R is an acyclic alkyl group having 6 to 12 carbon atoms, X is a divalent alkyl radical selected from the group of —CH$_2$—, —CH$_2$CH$_2$—, —CH$_2$CH(OH)—, —CH═CH— (cis or trans), or —CHOH—. Additionally, the dibasic ester can be employed in the form wherein the free carboxyl group is converted to the alkali metal, ammonium, or amine salt.

The second component of the composition is a surface active agent or emulsifier which serves in providing uniform dispersions of all formulation components of both solid and liquid types, and may be anionic, cationic, or non-ionic, and includes conventional soaps, such as the water-soluble salts of long chain carboxylic acids, the amine soaps such as the amine salts of long chain carboxylic acids, the sulfonated animal, vegetable and mineral oils, quaternary salts of high molecular weight acids, rosin soaps such as salts of abietic acid, sulfuric acid salts of high molecular weight organic bases, algin soaps, ethylene oxide condensed with fatty acids and/or sorbitol esters, alkyl phenols and mercaptans, and other simple as well as polymeric compositions having both hydrophilic and hydrophobic functions so as to enable the mixing of otherwise immiscible ingredients. Generally, the surface active agents will be only a minor portion of the formulation as used, for example, less than 10% and frequently as low as 0.05%. In general, concentrations of from 0.5 to 5% are found to be optimum. Typical useful emulsifiers by trade names and chemical description are as follows: Antarox A-401, alkylarylpolyoxyethyleneglycol ether; Nonisol 210, polyethyleneglycol oleate; Triton X-45, octyphenoxypolyethoxyethanol; polyoxyethylene condensates of sorbitan fatty esters, e.g., Tween 20, Tween 60; and polyethyleneglycolesters of fatty acids, e.g., Ethofat 60/25 and Kessco PEG-600 monostearate.

The acid esters may be used as plant growth regulants in the form of the free acids or their salts, such as, i.e., alkali metal, alkaline earth metal, ammonium or amine (substituted ammonium) salts, e.g., sodium, potassium, ammonium, methylammonium, dimethylammonium, trimethylammonium, ethylammonium, ethanolammonium, diethanolammonium, or triethanolammonium salts, since the salts give equivalent results. The salts may readily be formed directly from the acid and a selected base such as an alkali-metal hydroxide or carbonate, or ammonia, or an amine.

Examples of esters suitable for preparation of compositions of this invention include:

Octyl, decyl, and dodecyl esters of malic acid
Decyl ester of maleic acid
Decyl ester of succinic acid
Monodecyl ester, monodiethanolamine salt of succinic acid
Monodecyl ester, monodiethanolamine salt of malonic acid
Monodecyl ester, monopotassium salt of malonic acid
Monohexyl ester of succinic acid
Monohexyl ester of malic acid The compounds of the invention may be used for killing meristematic buds on ornamental and agricultural, herbaceous, semiwoody, and woody plants such as chrysanthemum, cotton, azalea, apple, and tobacco. Meristematic buds include both terminal and axillary buds. The selective killing of terminal buds is an application for which the chemicals of the invention are particularly useful.

The chemicals of the present invention may be applied to plants, which term includes various plant parts such as flowers, fruits, vegetables, roots, and foliage in various manners. In one embodiment of the invention, the composition is applied as an aqueous dispersion or emulsion. For example, the composition may be applied in a coarse water spray directed to the stem of the plant, and such spray application is found to give effective control. The chemicals may also be dissolved in organic solvents such as acetone, benzene, or kerosene (assuming these chemicals will not harm the plant), and the solutions of the chemicals emulsified in water with the aid of surface-active agents. The chemicals of the invention may be admixed with powdered solid carriers, such as mineral silicates, together with a surface-active agent so that a wettable powder may be obtained which may be applied directly to plants, or which may be shaken up with water for application to the plants in that form.

On a weight basis, the concentration of active chemical in the useful formulations (before dilution with water or other materials prior to application) may vary widely, e.g., from 5 to 50%. Generally, the active chemical in aqueous dispersions which are applied is from 0.025 to 4.0%, and best results have been obtained using concentrations of from about 0.05 to 2.0%. The amount of active chemical applied per acre may vary from 0.1 to 16 pounds depending on the plant being treated and other factors known to those skilled in the art.

In the killing of the meristematic tissue, a particularly advantageous embodiment of the invention is the use of a $C_6$ to $C_{12}$ alkyl alcohol in combination with the other chemicals of the composition. The resulting composition exhibit reduced phytotoxicity and good control of meristematic tissue while using lower concentrations of active ingredients. The amount of alcohol employed, based on the combined weight of the dibasic acid ester, surface active agent, and alcohol is from 40 to 80%.

Alcohols useful in the preparation of the compositions of this invention include hexanol, octanol, nonanol, decanol, undecanol, dodecanol, and mixtures thereof typified by commercially available products such as "Alfo 810" sold by Continental Oil Company, which is a mixture of octanols and decanols. Other useful alcohols are exemplified by mixtures ($C_7$ - $C_9$ - $C_{11}$) of alcohols sold under the designation of Oxo alcohols by the Monsanto Chemical Company. These alcohol mixtures contain, for example, about 30% branched chain compounds which are generally 2-methyl substituted alcohols. Suitable $C_7$ - $C_9$ - $C_{11}$ mixtures contain, for example, about 40% $C_7$, 40% $C_9$, and 20% $C_{11}$. The alcohols employed include both straight and branched-chain alcohols and can be derived from synthetic or natural sources, e.g., paraffins or fatty acids or their esters. As employed in the invention, the alcohols contain from 6 to 12 carbon atoms and preferably contain from 8 to 11 carbon atoms. It is understood that small amouts of impurities such as fatty acids and hydrocarbons may be present due to the method of preparation of the alcohols employed, but this is generally undesirable and should be minimized where possible. Also, alcohols having less than 6 and more than 12 carbon atoms can be used with some benefit and indeed are frequently present as impurities. Suitable fatty acid sources for alcohols include caproic acid, caprylic acid, capric acid, and lauric acid or their esters with the corresponding alcohol being produced by reduction by means well known in the art.

The following examples illustrate the application of compositions of the invention to tobacco plants. As applied, the compositions were in the form of aqueous emulsions. These were applied to tobacco plants in the early button to early flowering stages, by spraying tops and stems with a 3-nozzle sprayer, and allowing the emulsion to drain down along the stem of the plant where meristematic and differentiating tissues are destroyed through contact. The emulsions were applied at a rate of approximately 30 to 50 gallons per acre. After 7 to 14 days, the effectiveness of the spray treatment was determined observing for chemical topping and also by weighing the number of suckers remaining after treatment and comparing with the weight of suckers present in a control plot wherein the tobacco was untreated. The degree of sucker control was then expressed as the percentage formed by suckers from the treating plot as compared with suckers in the control plot, e.g., if the total weight of suckers from the treated plot was 25% less than the total sucker weight from the control plot, the degree of sucker control was 25%. Attention was also given to the degree of plant injury accompanying application of the sucker control agents of the invention. Injury was determined by visual estimate. Injury of 5% or less means that visual observation indicated only occasional necrotic light spotting on foliage of less than 5% of the plants. Light injury was spotting or browning on 5 - 20% of the plants. Moderate injury was roughly 20 to 50% spotting or browning, and heavy damage was considered to be anything in excess of 50%. The results of the applications described above are set forth in the Table.

TABLE

Summary of Tests on Tobacco

| Example | Composition | | Conc.% | Topping Action | Sucker Control(%) | Plant Injury(%) |
|---|---|---|---|---|---|---|
| 1 | monodecyl ester of malic acid | | 2.5 | Yes | 100 | 40–80 |
| | | | 1.0 | Yes | 100 | 0–75 |
| | | | 0.5 | Yes | 100 | 20 |
| | | | 0.25 | Yes | 100 | 20 |
| 2 | monodecyl ester of maleic acid | | 1.0 | Yes | 100 | 15–80 |
| | | | 0.5 | Yes | 20 | 10 |
| 3 | monodecyl ester of succinic acid | | 2.5 | Yes | 100 | 10–80 |
| | | | 1.0 | Yes | 95 | 75 |
| | | | 0.5 | Yes | 95 | 50 |
| | | | 0.25 | Yes | 100 | 10 |
| 4 | monodecyl ester, monodiethanolamine salt of succinic acid | | 0.5 | — | 70 | 5 |
| 5 | monodecyl ester, monodiethanolamine salt of malonic acid | | 0.5 | Yes | 80 | 0 |
| 6 | monodecyl ester, mono potassium salt of malonic acid | | 0.5 | — | 95 | 25 |
| 7 | monodecyl ester of malic acid<br>sorbitol ester<br>$C_{8-10}$ alcohol | 25%<br>5%<br>70% | 4.0 | Yes | 100 | 0 |
| 8 | monodecyl ester of maleic acid<br>sorbitol ester<br>$C_{8-10}$ alcohol | 45%<br>5%<br>50% | 1.0 | Yes | 95 | 0 |

In examples 7 and 8 above, the sorbitol ester was employed as an emulsifier. The particular ester employed was a condensation product of equal molar amounts of sorbitol and coconut fatty acid, together with about 20 moles of ethylene oxide. Such esters are widely available on a commercial basis, e.g., Armak Company sells sorbitan esters as Armotan PML-20. In examples 1 - 6, the composition contained, in addition to the chemicals listed, approximately 5% or less of an emulsifier, e.g., polyoxyethylene condensates of esters of sorbitol and oleic or lauric acid. The $C_8$ - $C_{10}$ alkyl alcohol employed in a number of the examples is available commercially as Alfo 810, a product of the Continental Oil Company. By "topping action" is meant that the top bud and adjacent young tender leaflets of the tobacco plant are killed. Topping action was present if 80% or more of the plants exhibited successful topping. Generally, application of the compositions of the invention resulted in topping 90% or more of the plants. In examples 4 and 6, the plants were not checked for topping action.

In examples 1, 2, and 3, a range of plant injury was noted particularly at the higher concentration levels. This is believed to be due primarily to non-uniform growth in the plants treated. Comparison of examples 1 and 2 with examples 7 and 8 illustrates that plant damage is substantially reduced by adding the aliphatic alcohol to the composition. In examples 8 and 9, sucker control and topping action are still maintained.

What is claimed is:

1. A composition for controlling the growth of suckers in tobacco plants, consisting essentially of:
    a. from about 5% to about 50% by weight of a member of the group consisting of a monoalkyl ester of an organic dicarboxylic acid of the formula:

HOOC —X— COOR wherein X is selected from the group consisting of —CH$_2$—, —CH$_2$CH$_2$—, —CH$_2$CH(OH)—, —CH=CH—, and —CHOH—, and R is alkyl having 6 to 12 carbon atoms, and the alkali metal, alkaline earth metal, ammonium, alkylammonium, and alkanolamine salts thereof;
    b. from about 0.05% to about 10% by weight of a surfactant; and
    c. from about 40% to about 80% of the total weight of the composition of an aliphatic alcohol having 6 to 12 carbon atoms.

2. A composition as in claim 1 wherein R is decyl.
3. A composition as in claim 1 wherein R is octyl.
4. A composition as in claim 1 wherein the ester is the decyl ester of maleic acid.
5. A composition as in claim 1 wherein the ester is the decyl ester of malic acid.
6. A composition as in claim 1 containing the decyl ester of succinic acid.
7. A composition as in claim 1 containing the monodiethanolamine salt of malonic acid wherein R is decyl.
8. A composition as in claim 1 containing the monodiethanolamine salt of succinic acid wherein R is decyl.
9. A composition as in claim 1 containing the monopotassium salt of malonic acid wherein R is decyl.
10. A composition as in claim 1 wherein the alcohol is a mixture of C$_8$ to C$_{10}$ alcohols.
11. A composition as in claim 1 wherein the alcohol is undecanol.
12. A composition as in claim 1 wherein the surface active agent is an ethylene oxide condensate with a sorbitol oleic or lauric acid ester.
13. A composition as in claim 1 wherein the alcohol is a mixture of C$_8$ to C$_{10}$ alcohols.
14. A composition as in claim 1 wherein the alkyl alcohol is a mixture of branched chain isomers of C$_{10}$ to C$_{11}$ alcohols.
15. A method for controlling sucker growth in tobacco plants which comprises applying to said plants an aqueous dispersion containing an effective amount for sucker control, of a concentrate consisting essentially of:
    a. from about 5% to about 50% by weight of a member of the group consisting of a monoalkyl ester of an organic dicarboxylic acid of the formula:

HOOC — X — COOR wherein X is selected from the group consisting of —CH$_2$—, —CH$_2$CH$_2$—, —CH$_2$CH(OH)—, —CH=CH—, and —CHOH—, and R is alkyl having 6 to 12 carbon atoms, and the alkali metal, alkaline earth metal, ammonium, alkylammonium, and alkanolamine salts thereof;
    b. from about 0.05% to about 10% by weight of a surfactant; and
    c. from about 40% to about 80% of the total weight of the concentrate of an aliphatic alcohol having 6 to 12 carbon atoms.

16. A method as in claim 15 where the alcohol is a mixture of C$_8$ to C$_{10}$ alcohols.
17. A method as in claim 15 where the alcohol is undecanol.

* * * * *